United States Patent [19]

Fujihara et al.

[11] Patent Number: 5,688,985
[45] Date of Patent: Nov. 18, 1997

[54] PROCESS FOR PRODUCING KETO NITRILE DERIVATIVE

[75] Inventors: Mitsuhiko Fujihara; Kenji Asahina; Toru Watanabe; Toshiyuki Takezawa; Seiji Watanabe, all of Shizuoka, Japan

[73] Assignee: Takasago International Corporation, Tokyo, Japan

[21] Appl. No.: 590,177

[22] Filed: Jan. 23, 1996

[30] Foreign Application Priority Data

Feb. 28, 1995 [JP] Japan .................. 7-063549

[51] Int. Cl.$^6$ .................. C07C 253/00; C07C 225/00
[52] U.S. Cl. .................. 558/311; 564/342; 564/343
[58] Field of Search .................. 558/311; 564/342, 564/343

[56] References Cited

U.S. PATENT DOCUMENTS 5,491,253  2/1996  Stuk et al. .................. 563/342 X

OTHER PUBLICATIONS

Stuk et al., J. Org. Chem., 59(15), 4040–4041 (1994).

*Primary Examiner*—Floyd D. Higel
*Attorney, Agent, or Firm*—Sughrue, Mion, Zinn, Macpeak & Seas, PLLC

[57] ABSTRACT

A process for producing a (4S)-4-(N,N-dibenzyl)amino-5-phenyl-3-oxo-pentanenitrile derivative which comprises reacting a (2S)-2-(N,N-dibenzyl)aminophenylalanine ester derivative with acetonitrile in the presence of a lithium compound or a magnesium compound is disclosed, and a process for producing a (2S)-2-(N,N-dibenzyl)amino-5-amino-1,6-diphenyl-4-hexen-3-one derivative which comprises adding a benzylmagnesium halide or a benzyllithium to a reaction solution containing the (4S)-4-(N,N-dibenzyl)amino-5-phenyl-3-oxo-pentanenitrile derivative and reacting the derivative with the benzylmagnesium halide or the benzyllithium is also disclosed. According to these processes, optically pure (4S)-4-(N,N-dibenzyl)amino-5-phenyl-3-oxo-pentanenitrile derivative and (2S)-2-(N,N-dibenzyl)amino-5-amino-1,6-diphenyl-4-hexen-3-one derivative can be produced in a good yield on an industrial scale.

4 Claims, No Drawings

PROCESS FOR PRODUCING KETO NITRILE DERIVATIVE

FIELD OF THE INVENTION

The present invention relates to a process for preparing an intermediate of a compound represented by formula (VII):

A—X—B          (VII)

wherein X represents a group represented by formula (VIII):

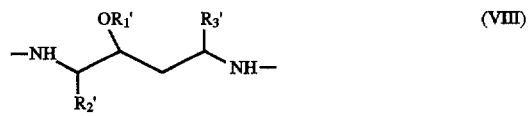

wherein $R_1'$ represents a hydrogen atom or a lower alkyl group; and $R_2'$ and $R_3'$ each represent an aralkyl group, a cycloalkyl group or an alkyl group; and A and B each represent $R_6'$—C(O)—(NH)—(CH($R_5'$))—(CO)— or $R_6'$—C(O)—, wherein $R_5'$ represents a lower alkyl group; and $R_6'$ represents $R_7'$—NH— or $R_7'$—N(lower alkyl)—, wherein $R_7'$ represents a (heterocyclic ring)-alkyl group, and a pharmaceutically acceptable salt or a prodrug thereof (JP-A-4-308574, the term "JP-A" as used herein means an "unexamined published Japanese patent application"; *J. Org. Chem.*, 59, 4040–4041 (1994)). The compound of formula (VII) inhibits retrovirus proteases, particularly HIV (human immunodeficiency virus) protease participating in growth and character expression of AIDS (acquired immunodeficiency syndrome) virus.

BACKGROUND OF THE INVENTION

It is known that the compound represented by formula (II), (4S)-4-(N,N-dibenzyl)amino-5-phenyl-3-oxo-pentanenitrile is synthesized by reacting β-phenylalanine with benzyl chloride in the presence of potassium carbonate to afford N,N-dibenzyl-β-phenylalanine benzyl ester (I) and condensing the ester with an acetonitrile carbanion prepared from acetonitrile and sodium amide, and further the compound represented by formula (VI), (2S)-2-(N,N-dibenzyl)amino-5-amino-1,6-diphenyl-4-hexen-3-one is synthesized by subjecting the compound represented by formula (II) to separation and condensing the compound with benzylmagnesium chloride in tetrahydrofuran, as shown in the following reaction scheme (*J. Org. Chem.*, 59, 4040–4041 (1994)):

Reaction Scheme:

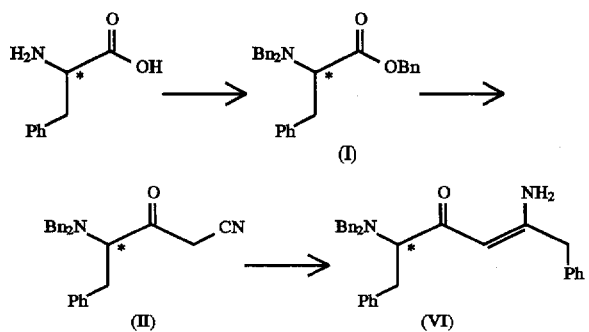

According to the present inventors' findings, in the industrial and economical mass production of a (4S)-4-(N,N-dibenzyl)amino-5-phenyl-3-oxo-pentanenitrile derivative (II), the above-described process is carried out according to the following procedure.

That is, a (2S)-2-(N,N-dibenzyl)aminophenylalanine ester derivative (I) is dissolved in a mixed solvent of tetrahydrofuran (THF) and acetonitrile, and the solution is cooled to −45° C. Separately, acetonitrile is added to the suspension of sodium amide at 45° C., and the solution is cooled to −45° C. and slowly added dropwise to the above prepared solution of phenylalanine derivative (I) in THF/acetonitrile at −45° C. After the addition, the reaction mixture is treated with a 25% aqueous solution of citric acid. The organic layer separated is washed twice with a saturated sodium chloride aqueous solution, and heptane is added thereto. The organic layer is further washed three times with a 5% sodium chloride aqueous solution and then twice with 10% methanolic water. Concentration of the final organic layer gives a (4S)-4-(N,N-dibenzyl)amino-5-phenyl-3-oxo-pentanenitrile derivative.

Throughout the above-mentioned procedure, that is, up to the end of the reaction, the optical purity of the starting material is maintained. However, it turned out that the reaction mixture undergoes partial racemization while it is worked up.

Generally, where a compound for use as a medicine has a chiral structure, cases are often met in which only one of the enantiomers exhibits a physiological activity with the other having no physiological activity. Further, cases sometimes occur in which some unfavorable physiological activity is exerted. It is therefore demanded that the compound be optically pure on use. It follows that intermediates for the compound should also be optically pure.

SUMMARY OF THE INVENTION

The object of the present invention is to provide a novel process for producing an optically pure (4S)-4-(N,N-dibenzyl)amino-5-phenyl-3-oxo-pentanenitrile derivative (II) in a good yield on an industrial scale without impairing the optical purity of a starting material.

Another object of the present invention is to provide a novel process for producing a (2S)-2-(N,N-dibenzyl)amino-5-amino-1,6-diphenyl-4-hexen-3-one derivative (VI) economically and in a large amount.

Considering the above-described situation, the present inventors have conducted extensive investigations into industrial synthesis of an optically pure (4S)-4-(N,N-dibenzyl)amino-5-phenyl-3-oxo-pentanenitrile derivative (II). As a result, they have found that an optically pure compound (II) can be prepared in a good yield without impairing the optical purity of a starting material by using a lithium compound or a magnesium compound as a reagent for generating a carbanion of acetonitrile. Further, the present inventors have found that a (2S)-2-(N,N-dibenzyl)amino-5-amino-1,6-diphenyl-4-hexen-3-one derivative (VI) can be obtained at one stage by reacting a carbanion of acetonitrile prepared from acetonitrile and a Grignard reagent with a (2S)-2-(N,N-dibenzyl)aminophenylalanine benzyl ester derivative (I) to provide an enolate of keto nitrile (II) as an intermediate, and then reacting the intermediate, without being treated with water for isolation, with a benzylmagnesium halide or a benzyllithium. The present invention has been completed based on these findings.

That is, the embodiments of the present invention are as follows:

(1) A process for producing a (4S)-4-(N,N-dibenzyl)amino-5-phenyl-3-oxo-pentanenitrile derivative represented by formula (II):

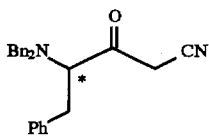

wherein Bn represents a benzyl group, Ph represents a phenyl group, and C* represents an asymmetric carbon atom, which comprises reacting a (2S)-2-(N,N-dibenzyl) aminophenylalanine ester derivative represented by formula (I):

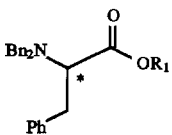

wherein $R_1$ represents a lower alkyl group or a benzyl group, and Bn, Ph and C* are as defined above, with acetonitrile in the presence of a lithium compound or a magnesium compound;

(2) The process as described in (1) above, wherein said lithium compound is an organolithium compound represented by formula (III):

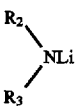

wherein $R_2$ and $R_3$, which may be the same or different, each represent a hydrogen atom, a lower alkenyl group, a phenyl group or a benzyl group, provided that they do not simultaneously represent a hydrogen atom, or they may be taken together to form a 5- or 6-membered ring together with a nitrogen atom;

(3) The process as described in (1) above, wherein said magnesium compound is an organomagnesium compound represented by formula (IV):

R₄MgX (IV)

wherein X represents a halogen atom and $R_4$ represents a lower alkyl group, an aralkyl group, a phenyl group or a vinyl group, or an organomagnesium compound represented by formula (V):

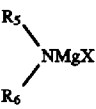

wherein X is as defined above and $R_5$ and $R_6$, which may be the same or different, each represents a hydrogen atom, a lower alkyl group, a lower alkenyl group, a phenyl group or a benzyl group, provided that they do not simultaneously represent a hydrogen atom, or they may be taken together to form a 5- or 6-membered ring together with a nitrogen atom;

(4) A process for producing a (2S)-2-(N,N-dibenzyl) amino-5-amino-1,6-diphenyl-4-hexen-3-one derivative represented by formula (VI):

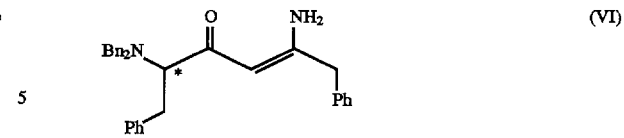

wherein Bn represents a benzyl group, Ph represents a phenyl group, and C* represents an asymmetric carbon atom, which comprises adding a benzylmagnesium halide or a benzyllithium to a reaction solution containing a (4S)-4-(N, N-dibenzyl)amino-5-phenyl-3-oxo-pentanenitrile derivative represented by formula (II):

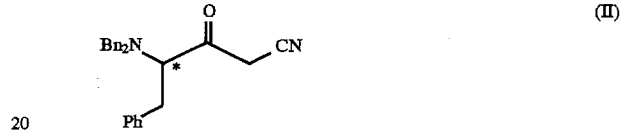

wherein Bn, Ph and C* are as defined above, and reacting the derivative represented by formula (II) with the benzylmagnesium halide or the benzyllithium; and (5) A process for producing a (2S)-2-(N,N-dibenzyl) amino-5-amino-1,6-diphenyl-4-hexen-3-one derivative represented by formula (VI):

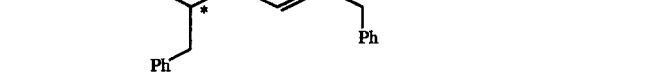

wherein Bn represents a benzyl group, Ph represents a phenyl group, and C* represents an asymmetric carbon atom, which comprises reacting a (2S)-2-(N,N-dibenzyl) aminophenylalanine ester derivative represented by formula (I):

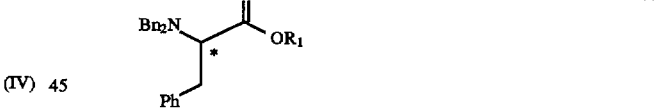

wherein $R_1$ represents a lower alkyl group or a benzyl group, and Bn, Ph and C* are as defined above, with acetonitrile in the presence of a benzylmagnesium halide or a benzyllithium.

DETAILED DESCRIPTION OF THE INVENTION

The present invention will be explained in more detail.

First, the case of using an organomagnesium compound as a carbanion generator will be explained.

A typical example of using the magnesium compound as a carbanion generator of acetonitrile is as follows.

That is, a (2S)-2-(N,N-dibenzyl)aminophenylalanine ester derivative (I) and acetonitrile are dissolved in THF, and the solution is added dropwise to a separately prepared THF solution of an organomagnesium reagent at 0° to 25° C., followed by stirring at room temperature for 1 to 5 hours. The addition order can be reversed, i.e., the addition of organomagnesium reagent to a solution of (2S)-2-(N,N-dibenzyl)aminophenylalanine is also acceptable. The reaction mixture is poured into an aqueous citric acid solution, and the mixture is extracted with a 2:1 mixed solvent of toluene and heptane. The organic layer is washed successively with methanolic water and water, followed by concentration to give an intended keto nitrile derivative (II).

In the condensation reaction at the case of using the magnesium compound of the present invention, acetonitrile is usually used in an amount of 1 to 1.5 equivalents, preferably 1.05 to 1.3 equivalents, to the β-phenylalanine ester derivative (I), and the organomagnesium compound reagent as a carbanion generator is used in an amount of 2 to 5 equivalents, preferably 2.5 to 2.7 equivalents, to the β-phenylalanine ester derivative (I).

The condensation reaction is carried out at a temperature of −40° to 40° C., preferably −20° to 30° C., for a period of 1 to 24 hours, preferably 2 to 4 hours.

Removal of the solvent by concentration after the completion of the reaction is conducted at a temperature of 10° to 60° C., preferably 10° to 50° C., for 1 to 8 hours, preferably 1 to 2 hours.

Solvents which can be suited for the condensation reaction using the organomagnesium reagent include ethereal solvents generally employed in a Grignard reaction, such as THF, 1,2-dimethoxyethane, diglyme, diisopropyl ether, and t-butyl methyl ether.

The organomagnesium compound which can be used as a carbanion generator in the present reaction is preferably organomagnesium compounds represented by formula (IV):

$$R_4MgX \qquad (IV)$$

wherein X represents a halogen atom and $R_4$ represents a lower alkyl group, an aralkyl group, a phenyl group or a vinyl group. The above-described organomagnesium compounds typically include methylmagnesium bromide, methylmagnesium chloride, methylmagnesium iodide, ethylmagnesium bromide, ethylmagnesium chloride, ethylmagnesium iodide, vinylmagnesium chloride, vinylmagnesium bromide, butylmagnesium bromide, t-butylmagnesium chloride, hexylmagnesium bromide, propylmagnesium bromide, propylmagnesium chloride, cyclohexylmagnesium chloride, cyclohexylmagnesium bromide, cyclopentylmagnesium bromide, cyclopentylmagnesium chloride, phenylmagnesium bromide, phenylmagnesium chloride, benzylmagnesium chloride, and benzylmagnesium bromide.

In addition to these Grignard reagents, organomagnesium compounds represented by formula (X):

(wherein $R_7$ and $R_8$, which may be the same or different, each represent a lower alkyl group, a benzyl group or a phenyl group, or they may be taken together to form a 5- or 6-membered ring), can also be used.

Organomagnesium compounds represented by formula (V):

(wherein $R_5$ and $R_6$, which may be the same or different, each represent a lower alkyl group, a lower alkenyl group, a benzyl group or a phenyl group, or they may be taken together to form a ring; and X represents a halogen atom), can also preferably be used in the present reaction.

Specific examples of the organomagnesium compounds include N,N-dimethylaminomagnesium chloride, N,N-dimethylaminomagnesium bromide, N,N-diethylaminomagnesium chloride, N,N-diethylaminomagnesium bromide, N,N-diphenylaminomagnesium chloride, N-methyl-N-phenylaminomagnesium chloride, piperidinomagnesium chloride, piperidinomagnesium bromide, pyrrolidinomagnesium chloride, and pyrrolidinomagnesium bromide.

Next, the case of using an organolithium compound as a carbanion generator will be explained.

Organolithium reagents which can be used as a carbanion generator in the present reaction include vinyl lithium, propyl lithium, N-isopropylaminolithium, N,N-diphenylaminolithium, N-methyl-N-phenylaminolithium and N-t-butylaminolithium.

In the case of using the organolithium reagent as a carbanion generator, suitable reaction solvents include hydrocarbons such as toluene and heptane, ether solvents such as those used for the above-described organomagnesium reagents, and hydrocarbon/ether mixed solvents.

With respect to the amount used of the organolithium reagents to the β-phenylalanine ester derivative (I), the temperature and time for the condensation reaction, and the temperature and time for concentration of the solvent after completion of the reaction, almost the same conditions as those in the case of using the above-described magnesium compound as a carbanion generator of acetonitrile can be applied.

Further, the present invention is to provide a process for producing (2S)-2-(N,N-dibenzyl)amino-5-amino-1,6-diphenyl-4-hexen-3-one derivative (VI) from (4S)-4-(N,N-dibenzyl)amino-5-phenyl-3-oxo-pentanenitrile derivative (II) in the presence of a benzyllithium, and a process for producing (2S)-2-(N,N-dibenzyl)amino-5-amino-1,6-diphenyl-4-hexen-3-one derivative (VI) which comprises reacting a (2S)-2-(N,N-dibenzyl)aminophenylalanine ester derivative (I) with acetonitrile in the presence of a benzylmagnesium halide or a benzyllithium.

Among organomagnesium compounds, a Grignard reagent is preferred. Use of a Grignard reagent as a carbanion generator has the following advantage. After a carbanion of acetonitrile is prepared from acetonitrile and a Grignard reagent, reaction between the carbanion and a (2S)-2-(N,N-dibenzyl)aminophenylalanine ester derivative (I) results in formation of an enolate of keto nitrile (II) as an intermediate, which can then be reacted, without being treated with water for isolation, with a benzylmagnesium halide to obtain a (2S)-2,5-diamino-1,6-diphenyl-4-hexen-3-one derivative (VI) at one stage.

EXAMPLES

The present invention will be illustrated in greater detail with reference to Examples and Comparative Examples, but the invention is not construed as being limited thereto.

1. Chemical purity of products obtained was determined by liquid chromatography under the following conditions:

Analytical instrument: High Performance Liquid Chromatography L-6000 (manufactured by Hitachi, Ltd.)
Column: Shodex C18-5B; 4.6×250 mm
Mobile phase: acetonitrile/water=9/1
Flow rate: 1.0 ml/min
Detection: 254 nm (UV)

2. Optical purity of products obtained was determined by liquid chromatography under the following conditions:

Analytical instrument: High Performance Liquid Chromatography LC-9A (manufactured by Shimadzu Corporation)

Column: Chiralcel OD-H; 4.6×250 mm

Mobile phase: hexane/isopropyl alcohol=7/3

Flow rate: 0.5 ml/min

Detection: 250 nm (UV)

3. The reaction was monitored by liquid chromatography under the above conditions.

4. The products obtained were identified by high performance liquid chromatography and $^1$H-NMR using the respective standard preparation prepared in a conventional manner (Timothy L. Stuk, et al., *J. Org. Chem.*, 59, 4040–4041 (1994)).

Comparative Example 1

In 1020 ml of toluene was suspended 80.2 g (2.06 mol) of sodium amide, and a solution of 340 g (781 mmol) of (2S)-2-(N,N-dibenzyl)aminophenylalanine benzyl ester and 42.7 g (1.04 mol) of acetonitrile in 550 ml of toluene was added dropwise to the suspension over a period of 1 hour. The mixture was stirred at 15° to 25° C. for 6 hours and poured into 1000 ml of 40% methanolic water containing 4N aqueous methanolic hydrochloric acid solution. The organic layer separated was washed successively with two 2250 ml portions of 30% methanolic water, two 1500 ml portions of water, and 30% THF/water. At this point, the product (4S)-4-(N,N-dibenzyl)amino-5-phenyl-3-oxo-pentanenitrile had an optical purity of 95.6%ee. On being allowed to stand at room temperature overnight, the product reduced its optical purity to 93.18%ee.

On concentration under reduced pressure at 40° to 50° C., the optical purity was further reduced to 74.1%ee.

Comparative Example 2

In 20 ml of THF was suspended 6.94 g (178 mmol) of sodium amide, and a mixed solution of 29.8 g (68.4 mmol) of (2S)-2-(N,N-dibenzyl)aminophenylalanine benzyl ester and 3.65 g (89.0 mmol) of acetonitrile was added dropwise to the suspension. The reaction solution was stirred at not more than 0° C. for 2 hours and poured into 100 ml of a 4N sulfuric acid solution to neutralize the solution, and then was extracted with a mixed solvent of 150 ml of toluene and 75 ml of heptane. This extract was washed with 40% methanolic water and water. At this stage, the product keto nitrile has an optical purity of 99.0%ee. When this was allowed to stand at 30° C. for 90 hours, the product reduced its optical purity to 94.9%ee for racemization. When it was further allowed to stand for one more day, the product reduced its optical purity to 91.7%ee for racemization.

Reference Example 1

A solution of 94 mmol of lithium diethylamide in 100 ml of THF was cooled to 10° C. or lower. A solution of 18.5 g (42 mmol) of (2S)-2-(N,N-dibenzyl)aminophenylalanine benzyl ester and 3.38 g (82.4 mmol) of acetonitrile in 50 ml of THF was added thereto dropwise. After the addition, the mixture was stirred at 0° to 5° C. for 30 minutes and poured into 200 ml of a 2N hydrochloric acid aqueous solution, followed by extraction with 300 ml of toluene. After liquid-liquid separation, the organic layer separated was washed successively with 50 ml of water, 50 ml of a 5% aqueous solution of sodium hydrogencarbonate, and 50 ml of water.

At this point, the optical purity of the product was 100%ee. The resulting toluene solution was concentrated under reduced pressure of 15 to 5 mmHg at 60° C. or lower over 7 hours. After the concentration, the optical purity of the product was 98%ee. Recrystallization of the concentrate from 20 ml of butanol gave 9.26 g (59.3%) of (4S)-4-(N,N-dibenzyl)amino-5-phenyl-3-oxo-pentanenitrile having an optical purity of 98%ee.

Reference Example 2

Lithium diethylamide prepared from 18.8 g (2.68 mol) of lithium, 794 g (10.87 mol) of diethylamine, and 467 g (purity 78%, net 364 g, 2.67 mol) of myrcene was added dropwise at 10° C. or lower to a solution of 500 g (1.15 mol) of (2S)-2-(N,N-dibenzyl)aminophenylalanine benzyl ester and 61.3 g (1.49 mol) of acetonitrile in a mixed solvent of 1670 ml of toluene and 833 ml of heptane. After the dropwise addition, the mixture was stirred for 30 minutes and poured into 3300 ml of a 4N sulfuric acid aqueous solution. The toluene layer separated was washed successively with two 2500 ml portions of 40% methanolic water and 2000 ml of water, followed by recrystallization from 1100 ml of butanol to yield 341 g (80.2%) of the intended product (4S)-4-(N,N-dibenzyl)amino-5-phenyl-3-oxo-pentanenitrile. The optical purity of the product was found to be 100%ee.

Example 1

A solution of 50 g (115 mmol) of (2S)-2-(N,N-dibenzyl) aminophenylalanine benzyl ester and 6.12 g (149 mol) of acetonitrile in 32 ml of THF was added dropwise to a solution of 420 mmol of t-butylmagnesium chloride in 150 ml of THF at 0° C. The mixture was warmed to room temperature, at which it was stirred for 3 hours and then poured into a 11% citric acid aqueous solution. The organic layer separated was extracted with a mixed solvent of 400 ml of toluene and 200 ml of heptane. After liquid-liquid separation, the organic layer was washed successively with two portions of 40% methanolic water and two 200 ml portions of water, followed by concentration. At this point, the product had an optical purity of 100%ee. The concentrate was recrystallized from 100 ml of butanol to give 37.7 g (88.9%) of the intended product (4S)-4-(N,N-dibenzyl) amino-5-phenyl-3-oxo-pentanenitrile. The optical purity of the product was found to be 100%ee.

Reference Example 3

A solution of 16 g (36.7 mmol) of (2S)-2-(N,N-dibenzyl) aminophenylalanine benzyl ester and 1.96 g (47.8 mmol) of acetonitrile in 32 ml of THF was added dropwise to a solution of 161.7 mmol of benzylmagnesium chloride in 100 ml of THF at −10° C. or lower. The mixture was stirred at −15° C. for 1.5 hours and then poured into 336 g of a 8% citric acid aqueous solution, followed by extraction with a mixed solvent of 400 ml of toluene and 200 ml of heptane. The organic layer separated was washed successively with two 100 ml portions of 20% methanolic water and two 100 ml portions of water, followed by concentration. At this point, the product had an optical purity of 100%ee. The concentrate was recrystallized from 43 ml of butanol to give 10.7 g (79.1%) of the intended product (4S)-4-(N,N-dibenzyl)amino-5-phenyl-3-oxopentanenitrile. The optical purity of the product was 100%ee.

Example 2

A solution of 50 g (115 mmol) of (2S)-2-(N,N-dibenzyl) aminophenylalanine benzyl ester and 4.95 g (121 mmol) of acetonitrile in 100 ml of THF was added dropwise to a solution of 917 mmol of benzylmagnesium chloride in 300 ml of THF at −10° C. to −15° C. The mixture stirred at that temperature for 2.5 hours and then at 5° C. for 15 hours. THF was recovered under reduced pressure, 250 ml of toluene was added to the residue, and the solution was poured into a 22% citric acid aqueous solution. The reaction mixture was washed with three 250 ml portions of water. The organic layer separated was concentrated and recrystallized from 165 ml of ethanol to afford 34 g (58%) of the intended product (2S)-2-(N,N-dibenzyl)amino-5-amino-1,6-diphenyl-4-hexen-3-one. The optical purity of the product was 100%ee.

According to the process of the present invention, optically pure (4S)-4-(N,N-dibenzyl)amino-5-phenyl-3-oxo-pentanenitrile derivatives (II) and (2S)-2-(N,N-dibenzyl) amino-5-amino-1,6-diphenyl-4-hexen-3-one derivatives (VI) can be produced in a good yield on an industrial scale.

Further, among the organic magnesium compounds, when a Grignard reagent is used as a carbanion generator, a (2S)-2-(N,N-dibenzyl)amino-5-amino-1,6-diphenyl-4-hexen-3-one derivative (VI) can be produced at one stage by reacting a carbanion of acetonitrile prepared from acetonitrile and the Grignard reagent with a (2S)-2-(N,N-dibenzyl) aminophenylalanine ester derivative (I) to provide an enolate of keto nitrile (II) as an intermediate, and then reacting the intermediate, without being treated with water for isolation, with a benzylmagnesium halide.

While the invention has been described in detail and with reference to specific embodiments thereof, it will be apparent to one skilled in the art that various changes and modifications can be made therein without departing from the spirit and scope thereof.

What is claimed is:

1. A process for producing a (4S)-4-(N,N-dibenzyl) amino-5-phenyl-3-oxo-pentanenitrile derivative represented by formula (II):

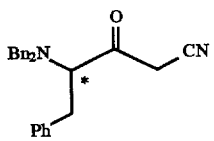

wherein Bn represents a benzyl group, Ph represents a phenyl group, and C* represents an asymmetric carbon atom, which comprises reacting a (2S)-2-(N,N-dibenzyl aminophenylalanine ester derivative represented by forumla (I):

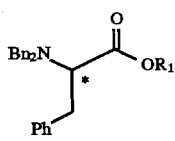

wherein $R_1$ represents a lower alkyl group or a benzyl group, and Bn, Ph and C* are as defined above, with acetonitrile in the presence of a lithium compound or a magnesium compound, wherein said lithium compound is an organolithium compound represented by formula (III):

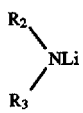

wherein $R_2$ and $R_3$, which are the same or different, each represent a hydrogen atom, a lower alkenyl group, a phenyl group or a benzyl group, provided that they do not simultaneously represent a hydrogen atom, or when taken together form a 5- or 6-membered ring together with a nitrogen atom.

2. A process for producing a (2S)-2-(N,N-dibenzyl) amino-5-amino-1,6-diphenyl-4-hexen-3-one derivative represented by formula (VI):

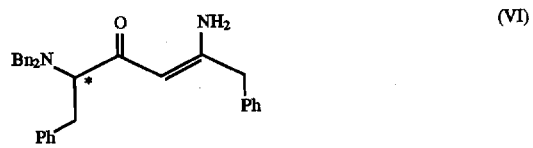

wherein Bn represents a benzyl group, Ph represents a phenyl group, and C* represents an asymmetric carbon atom, which comprises reacting a (2S)-2-(N,N-dibenzyl) aminophenylalanine ester derivative represented by formula (I):

wherein $R_1$ represents a lower alkyl group or a benzyl group, and Bn, Ph and C* are as defined above, with acetonitrile in the presence of a benzylmagnesium halide or a benzyllithium.

3. A process for producing a (4S)-4-(N,N-dibenzyl) amino-5-phenyl-3-oxo-pentanenitrile derivative represented by formula (II):

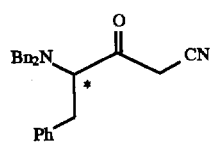

wherein Bn represents a benzyl group, Ph represents a phenyl group, and C* represents an asymmetric carbon atom, which comprises reacting a (2S)-2-(N,N-dibenzyl aminophenylalanine ester derivative represented by forumla (I):

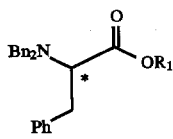

wherein $R_1$ represents a lower alkyl group or a benzyl group, and Bn, Ph and C* are as defined above, with acetonitrile in the presence of a lithium compound or a magnesium compound, wherein said lithium compound is an organolithium compound represented by formula (III):

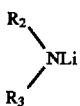
(III)

wherein $R_2$ and $R_3$, which are the same or different, each represent a hydrogen atom, a lower alkenyl group, a phenyl group or a benzyl group, provided that they do not simultaneously represent a hydrogen atom, or when taken together form a 5- or 6-membered ring together with a nitrogen atom and wherein said magnesium compound is an organomagnesium compound represented by formula (IV):

$$R_4MgX \quad (IV)$$

wherein X represents a halogen atom and $R_4$ represents a lower alkyl group, an aralkyl group, a phenyl group or a vinyl group, or an organomagnesium compound represented by formula (V):

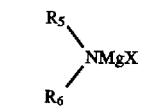
(V)

wherein X is as defined above and $R_5$ and $R_6$, which are the same or different, each represents a hydrogen atom, a lower alkyl group, a lower alkenyl group, a phenyl group or a benzyl group, provided that they do not simultaneously represent a hydrogen atom, or when taken together form a 5- or 6-membered ring together with a nitrogen atom.

4. The process as claimed in claim 3, wherein the reacting with acetonitrile is in the presence of the magnesium compound.

* * * * *